United States Patent
Katiyar et al.

(10) Patent No.: US 11,926,540 B2
(45) Date of Patent: Mar. 12, 2024

(54) CYCLE WATER TREATMENT PROCESS FOR ETHLYENE EPOXIDATION

(71) Applicant: Scientific Design Company, Inc., Little Ferry, NJ (US)

(72) Inventors: Saurabh Katiyar, Little Ferry, NJ (US); Saurabh H. Parikh, Little Ferry, NJ (US); Jason P. Durand, Wyckoff, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 63 days.

(21) Appl. No.: 17/686,556

(22) Filed: Mar. 4, 2022

(65) Prior Publication Data

US 2022/0281757 A1    Sep. 8, 2022

Related U.S. Application Data

(60) Provisional application No. 63/157,238, filed on Mar. 5, 2021.

(51) Int. Cl.
| | | |
|---|---|---|
| *C02F 1/42* | (2023.01) | |
| *C02F 101/34* | (2006.01) | |
| *C02F 103/36* | (2006.01) | |
| *C07D 303/04* | (2006.01) | |

(52) U.S. Cl.
CPC .............. *C02F 1/42* (2013.01); *C07D 303/04* (2013.01); *C02F 2001/422* (2013.01); *C02F 2101/34* (2013.01); *C02F 2103/36* (2013.01)

(58) Field of Classification Search
CPC .. C02F 1/42; C02F 2001/422; C02F 2101/34; C02F 2103/36; C07D 303/04
See application file for complete search history.

(56) References Cited

U.S. PATENT DOCUMENTS

| | | | |
|---|---|---|---|
| 3,563,914 A | 2/1971 | Wattimena | |
| 3,702,259 A | 11/1972 | Nielsen | |
| 4,289,593 A * | 9/1981 | Briody | C07C 29/76 204/157.9 |
| 4,376,209 A | 3/1983 | Watanabe et al. | |
| 4,761,394 A | 8/1988 | Lauritzen | |
| 4,766,105 A | 8/1988 | Lauritzen | |
| 4,822,926 A | 4/1989 | Dye | |
| 4,908,343 A | 3/1990 | Bhasin | |
| 5,011,807 A | 4/1991 | Hayden et al. | |
| 5,034,134 A | 7/1991 | George et al. | |
| 5,057,481 A | 10/1991 | Bhasin | |
| 5,099,041 A | 3/1992 | Hayden et al. | |
| 5,102,848 A | 4/1992 | Soo et al. | |
| 5,187,140 A | 2/1993 | Thorsteinson et al. | |
| 5,407,888 A | 4/1995 | Herzog et al. | |
| 5,440,058 A * | 8/1995 | Hoffman | B01J 19/002 568/920 |
| 6,187,973 B1 | 2/2001 | Husain | |
| 7,294,317 B2 | 11/2007 | Billig et al. | |
| 2007/0037991 A1 | 2/2007 | Rizkalla | |
| 2013/0331618 A1 | 12/2013 | Liu et al. | |
| 2018/0044309 A1 * | 2/2018 | McGovern | C07D 301/32 |
| 2019/0330132 A1 * | 10/2019 | Yamada | C07C 29/152 |
| 2020/0148655 A1 | 5/2020 | Duff et al. | |

OTHER PUBLICATIONS

Ethylene Glycol Purification by Melt Crystallization: Removal of short-chain glycol impurities, Wang et al., I&EC, 59, 8805-8812 (Year: 2020).*
Identification of impurities affecting commercial ethylene glycol UV transmittance, Zhang et al., Journal of Chromatography A, 904, 87-97 (Year: 2000).*
On-line sample clean up of fermentation broths and substrates prior to the liquid chromatographic separation of carbohydrates, Marko-Varga et al, Journal of Chromatography, 523, 173-188 (Year: 1990).*
Jiangsu Linhai Resin Science and Technology Co., Ltd, LH-113 Macroporous Acrylic type weakly acid exchange resin (Year: 2016).*
Singare, Non-destructive radioanalytical technique in characterization of anion exchangers Amberlite IRN78 and Indion H-IP, J Radioanal Nucl Chem 299:591-598 (Year: 2014).*
Amberlite(TM) IRN78 OH hydroxide form, Millipore Sigma (Year: 2023).*
Brunauer, S., et al., "Adsorption of Gases in Multimolecular Layers", J. Am. Chem. Soc., Feb. 1938, pp. 309-316.
International Search Report dated May 11, 2022, 9 pages.

* cited by examiner

*Primary Examiner* — Matthew P Coughlin
*Assistant Examiner* — Meghan C Heasley
(74) *Attorney, Agent, or Firm* — Scully, Scott, Murphy & Presser, P.C.

(57) ABSTRACT

A method for the oxidation of ethylene to form ethylene oxide which comprises
treating an aqueous stream in a cycle water treatment unit containing an anion exchange resin to reduce the content of the impurities.

11 Claims, 4 Drawing Sheets

US 11,926,540 B2

CYCLE WATER TREATMENT PROCESS FOR ETHLYENE EPOXIDATION

CROSS REFERENCE TO RELATED APPLICATION

The present invention claims the benefit of U.S. Provisional Patent Application No. 63/157,238, filed Mar. 5, 2021, the entire content and disclosure of which is incorporated herein by reference.

FIELD OF THE INVENTION

The present invention relates to a method for the oxidation of ethylene into ethylene oxide.

BACKGROUND OF THE INVENTION

Though present in natural settings at minute quantities, ethylene oxide was first synthesized in a laboratory setting in 1859 by French chemist Charles-Adolphe Wurtz using the so-called "chlorohydrin" process. However, the usefulness of ethylene oxide as an industrial chemical was not fully understood in Wurtz's time; and so industrial production of ethylene oxide using the chlorohydrin process did not begin until the eve of the First World War due at least in part to the rapid increase in demand for ethylene glycol (of which ethylene oxide is an intermediate) as an antifreeze for use in the rapidly growing automobile market. Even then, the chlorohydrin process produced ethylene oxide in relatively small quantities and was highly uneconomical.

The chlorohydrin process was eventually supplanted by another process, the direct catalytic oxidation of ethylene with oxygen, the result of a second breakthrough in ethylene oxide synthesis, discovered in 1931 by another French chemist Thèodore Lefort. Lefort used a solid silver catalyst with a gas phase feed that included ethylene and utilized air as a source of oxygen.

In the eighty years since the development of the direct oxidation method, the production of ethylene oxide has increased so significantly that today it is one of the largest volume products of the chemicals industry, accounting, by some estimates, for as much as half of the total value of organic chemicals produced by heterogeneous oxidation. Worldwide production in the year 2000 was about 15 billion tons. (About two thirds of the ethylene oxide produced is further processed into ethylene glycol, while about ten percent of manufactured ethylene oxide is used directly in applications such as vapor sterilization.)

The growth in the production of ethylene oxide has been accompanied by continued intensive research on ethylene oxide catalysis and processing, which remains a subject of fascination for researchers in both industry and academia. Of particular interest in recent years has been the proper operating and processing parameters for the production of ethylene oxide using so-called "high selectivity catalysts", that is, Ag-based epoxidation catalysts that are especially efficient at catalyzing the desired product reaction of ethylene and oxygen to ethylene oxide rather than the side reaction of ethylene and oxygen, which produces carbon dioxide byproduct (and water).

However, while high selectivity catalysts have reduced the formation of carbon dioxide byproduct, they may also have increased the production of other undesired byproducts, notably aldehydic impurities such as acetaldehydes and formaldehydes ("aldehydes") and their associated acids as well as dissociated ions. Acetaldehyde and formaldehyde have long been known as byproducts formed during the operation of ethylene oxide plants. Acetaldehyde is formed as a result of the isomerization of ethylene oxide, while formaldehyde is formed by the reaction of ethylene oxide with oxygen. The associated acids, acetic acid and formic acid, are produced by oxidizing acetaldehyde and formaldehyde, respectively. The presence of these impurities can negatively affect the quality of the ethylene glycol solution and thereby cause degradation of the fiber grade ethylene glycol product. Additionally, the formation of their associated acids (as well as their aldehydic reagents) can decrease the pH to levels sufficiently low to cause corrosion in the plant. These considerations are even more serious in plants that produce fiber grade ethylene glycol. It is additionally important to note that while an impurity like carbon dioxide is produced almost exclusively on the catalyst bed in the ethylene oxide (EO) reactor, acetaldehydes, formaldehydes and their associated acids are produced both on the catalyst bed in the reactor and downstream of the reactor across several different columns and services in an EO plant.

One possible method of preventing or reducing the corrosion caused by acidic pH levels is to replace the carbon steel components with stainless steel components. While this is highly effective in at least reducing the rate of corrosion if not completely preventing it, using stainless steel components adds some expense and generally cannot be retrofitted into an existing plant. Moreover, this of course does not address the problem of low ethylene glycol product quality resulting from contamination by impurities.

Another possible solution is disclosed in U.S. Pat. No. 4,822,926 in which the reactor product stream is supplied to a quench section (the quench section being disposed inside the EO absorber), and in the quench section the reactor product stream is contacted with a base-containing recirculating aqueous solution in order to neutralize the pH and eliminate some of the organics. The addition of a base, like e.g., sodium hydroxide, does increase the pH (and as a consequence reduces the corrosion in the plant) as well as prevent the formation of some of the organics and aldehydic impurities. But the addition of caustic also frequently causes the decomposition and degradation of the ethylene glycol product, especially for heavier ethylene glycols like triethylene glycol, which often cannot be manufactured to meet minimum quality standards in a process utilizing caustic. Thus, in the end, caustic addition merely exchanges one problem (corrosion and impurity formation) for another (poor product quality).

Other technologies have also been developed in an attempt to reduce the formation of acetaldehyde and formaldehyde and associated impurities. For example, it has long been known that the isomerization of ethylene oxide to various aldehyde species occurs more readily at higher temperatures. This problem can be particularly pronounced as the product effluent leaves the reactor outlet at high temperatures and is largely maintained at such temperatures until entering a heat exchanger in order to cool the gas prior to its delivery to the absorption section.

Thus, techniques and equipment designs have been developed to reduce the temperature of the ethylene-containing product gas as quickly as possible. U.S. Pat. No. 4,376,209 discloses the use of inerts in a cooling zone of the reactor to cool the gas, however, as the '209 patent makes clear, this technique produced mixed results, and possibly actually increases acetaldehyde production as much as suppressing its formation.

Another approach is the integrated reactor-cooler assembly disclosed in U.S. Pat. No. 7,294,317, which is designed to bring about a sharp drop in the temperature of the ethylene-containing gas. However, while the integrated reactor-cooler has shown itself to be extremely successful at reducing the formation of byproducts, it fails to address those impurities that are generated at later processing stages. Moreover if not part of a new plant design, an extensive retrofit and revamp is necessary in order to accommodate the reactor-cooler assembly described in this patent making this approach far less applicable to existing plants.

The use of ion exchange resins requires less reworking for already-existing plants than the integrated reactor-cooler assembly and are highly efficacious at eliminating aldehydic and other impurities from the cycle water. Suitable ion exchange resins are such as those disclosed in U.S. Pat. No. 6,187,973. The ion exchange resins disclosed in the '973 patent are very effective at removing the non-dissociable organic impurities, especially aldehyde, from the cycle water, without causing the negative consequences mentioned above from caustic treatment. However, typically such resin cannot function alone because it has limited capacity to remove and treat ion exchangeable organic acids and ions and so is typically paired in a train with other resins that can uptake such impurities in the cycle water.

Thus, while the use of ion exchange cycle remediation remains the superior technique, still further improvements in the operation and composition such resins will result in significant improvements in product quality and operational efficiency and so are continually sought.

BRIEF SUMMARY OF THE INVENTION

The present invention relates to a method for removing impurities from an ethylene oxide manufacturing plant, which comprises providing an aqueous bleed stream comprising 0.2 to 20 wt % ethylene glycol and having a first UV 220 nm transmittance and introducing the aqueous bleed stream to a cycle water treatment unit containing an anion exchange resin to reduce the content of impurities in the aqueous feed stream, wherein the outlet of the cycle water treatment unit has a second UV 220 nm transmittance and the second UV 220 nm transmittance is higher than the first UV 220 nm transmittance.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings:

FIG. 7 shows the 220 nm transmittance values of FIG. 3 with the addition of conductivity data measured and plotted for comparison, and.

DETAILED DESCRIPTION OF THE INVENTION

Figure 1:
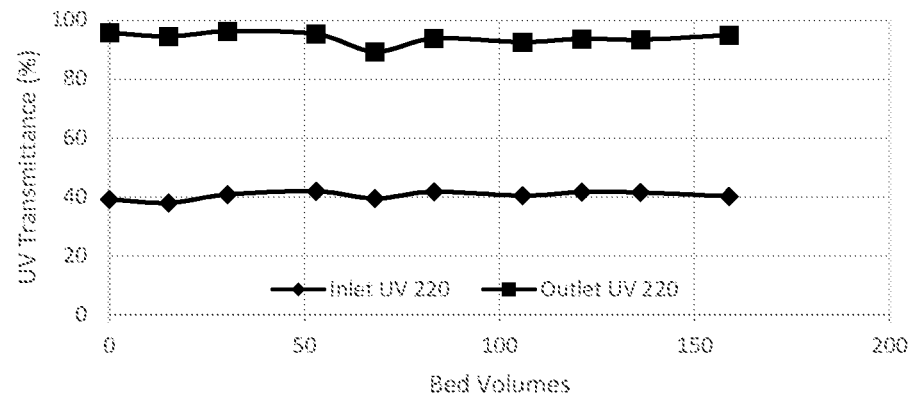
FIG. 1 shows the 220 nm transmittance values of the aqueous bleed stream measured at the inlet and outlet of a cycle water treatment unit in an ethylene oxide/ethylene glycol plant capable of annual production of greater than 250,000 MT EOE ("ethylene oxide equivalent").

All parts, percentages and ratios used herein are expressed by volume unless otherwise specified. All documents cited herein are incorporated by reference.

By "ion exchange resin" it is meant any conventional ion exchange resin, as known to a skilled person and, which is a readily-available article of commerce.

It has been found in the present invention that product quality can be improved by use of a process that is especially focused on removing impurities in the ethylene glycol product that absorb UV and reduce transmittance at the 220 nm wavelength. By the present invention, it has been found that a majority of the impurities in EO process streams that impair the quality of the final ethylene glycol product showed high absorbance at the UV 220 nm wavelength. By contrast at other commonly measured UV wavelengths, such as 350 nm, there are high transmittances—even of process streams with high quantities of quality-impairing impurities. Thus, by measuring and controlling the UV 220 nm transmittance of process steams in the ethylene oxide production process, final ethylene glycol product quality can be improved. For this purpose it has been found that anionic resins, especially strong base anionic resins are especially good at the removal of UV 220 absorbing impurities.

The use of this invention will now be described below in greater detail, below, as a component of an ethylene oxide production process.

Ethylene oxide is produced by continuously contacting an oxygen-containing gas with an olefin, preferably ethylene, in the presence of an ethylene oxide ("epoxidation") catalyst (described in greater detail below). By way of example, typical reactant feed mixtures under operating conditions may contain from about 0.5% to about 45%, preferably about 5% to about 30% of ethylene and from about 3% to about 15% oxygen, with the balance comprising comparatively inert materials including such substances as carbon dioxide, water, inert gases, other hydrocarbons, and the reaction moderators described herein. Non-limiting examples of inert gases include nitrogen, argon, helium and mixtures thereof. Non-limiting examples of the other hydrocarbons include methane, ethane, propane and mixtures thereof. Carbon dioxide and water are byproducts of the epoxidation process as well as common contaminants in the feed gases. Both have adverse effects on the catalyst, so the concentrations of these components are usually kept at a minimum.

Also present in the reaction, as previously mentioned, are one or more reaction moderators, non-limiting examples of which include organic halogen-containing compounds such as $C_1$ to $C_8$ halohydrocarbons; especially preferred are chloride-containing moderators such as methyl chloride, ethyl chloride, ethylene dichloride, vinyl chloride or mixtures thereof. Controlling chloride concentration level is particularly important with rhenium-containing catalysts.

As mentioned above, a usual method for the ethylene epoxidation process comprises the vapor-phase oxidation of ethylene with molecular oxygen, in the presence of an epoxidation catalyst, in a fixed-bed tubular reactor. Conventional, commercial fixed-bed ethylene-oxide reactors are typically in the form of a plurality of parallel elongated tubes (in a suitable shell) approximately 0.7 to 2.7 inches O.D. and 0.5 to 2.5 inches I.D. and 15-53 feet long, each filled and packed with catalyst. The reaction feed mixture (described above) is introduced into these tubes, and the resulting reactor effluent gas contains ethylene oxide, un-used reactants, and byproducts.

For purposes of illustration only, the following are conditions that are often used in current commercial ethylene oxide reactor units: a gas hourly space velocity (GHSV) of 1500-10,000 $h^{-1}$, a reactor inlet pressure of 150-400 psig, a coolant temperature of 180-315° C., an oxygen conversion level of 10-60%, and an EO production rate (work rate) of 7-20 lbs. EO/cu.ft. catalyst/hr. The feed composition in the reactor inlet after the completion of start-up and during normal operation typically comprises (by volume %) 1-40% ethylene, 3-12% $O_2$; 0.3% to 20%, preferably 0.3 to 5%, more preferably 0.3 to 1% of $CO_2$; 0-3% ethane, an amount of one or more chloride moderators, which are described herein; and the balance of the feed being comprised of argon, methane, nitrogen or mixtures thereof.

Typical operating conditions for the ethylene epoxidation process involve temperatures in the range from about 180° C. to about 330° C., and preferably, from about 200° C. to about 325° C., and more preferably from about 225° C. to about 280° C. The operating pressure may vary from about atmospheric pressure to about 30 atmospheres, depending on the mass velocity and productivity desired. Higher pressures may be employed within the scope of the invention. Residence times in commercial-scale reactors are generally on the order of about 2 to about 20 seconds.

The reactor effluent exits through the reactor outlet, is cooled and flows to the EO scrubbing column, where the reactor effluent is contacted with recirculated lean cycle water to absorb the ethylene oxide from the reactor effluent, forming rich cycle water. This rich cycle water is then fed to the EO stripping column for the recovery of the ethylene oxide. In the EO stripping column, the ethylene oxide is stripped out and the ethylene oxide vapor is sent overhead to a second EO absorber. The liquid water flows through the stripping column bottoms (referred to herein as the "lean cycle water") and a bleed stream is taken from the lean cycle water before the lean cycle water is returned to the EO scrubber where it is used to absorb ethylene oxide. This bleed stream is an aqueous stream that comprises about 0.2 to 20 wt % ethylene glycol, about 80 to 99.7 wt % water, and about 100 ppm to 1.0 wt % impurities. Impurities can include, inter alia, aldehydic impurities such as formaldehyde, acetaldehyde, glycolaldehyde, their associated acids and ions, as well as their reaction products, such as long-chain esters that are produced as a result of the reaction of aldehydic impurities with ethylene oxide and/or ethylene glycol. This aqueous bleed stream from the cycle water is then sent to a cycle water treatment unit. Prior to being sent to the cycle water treatment unit, the UV transmittance of the aqueous bleed stream is measured at least at the 220 nm wavelength, "first UV 220 nm transmittance", and optionally be measured at additional wavelengths such as 350 nm wavelength, "first UV 350 nm transmittance".

The cycle water treatment unit contains one or more ion exchange treatment beds or resins. (In this application a "bed" contains an ion exchange resin.) The one or more ion exchange treatment beds contain at least one anion exchange resin. The one or more ion exchange treatment beds can be operated and organized either as a train or individually, although it is preferred that they be operated as a train. Each ion exchange bed is selected from either an anionic or cationic ion exchange bed, or possibly instead substituted with another adsorbent bed of another material as described elsewhere herein. It has been discovered in the present invention that anionic ion exchange resins, in particular strong base anionic exchange resins, are particularly effective at removing ions, aldehydes and their associated acids, and other UV 220 absorbing impurities. Thus, these resins not only exchange the dissociated ions and inorganic salts and organic acids, but they additionally absorb organic molecules, especially aldehydes. This makes unnecessary a separate ion exchange resin or bed specifically dedicated to removing aldehydes. The physical mechanisms making this versatility possible are described in greater detail below in the section dedicated to ion exchange resins.

The aqueous bleed stream is contacted with this ion exchange resin in the cycle water treatment unit at temperatures of from about 30° C. to about 50° C. although higher or lower temperatures may be used. Atmospheric pressure is preferred, but higher pressures can also be used depending on whether a pressure differential in the next processing unit is desired. Illustrative flow rates are about 1 to 10 volumes of solution per volume of resin per hour although this can vary widely. An analyzer is placed on the outlet (and preferably also the inlet) of each ion exchange treatment bed to measure the UV transmittance of the aqueous stream to determine the approximate concentration of ions and impurities in the outlet. (Redundant analyzers measuring the pH or conductivity may also be utilized.) These measurement techniques, which are discussed in greater detail below, are used to determine whether "breakthrough" of the impurities has occurred. Breakthrough occurs when many or most of the functional groups on the active sites on an ion exchange resin have been exchanged with target ions or impurities and thus, the ion exchange treatment bed no longer has sufficient capacity to absorb all of the impurities from the aqueous stream, leaving some measurable concentration of impurities to pass over the ion exchange resin "uncaptured" into the outlet stream. As some small concentrations of impurities is always able to pass through the ion exchange treatment bed, in the present invention breakthrough is defined not at full transmittance, but rather as defined below in Table 1.

Once out of the cycle water treatment unit, the treated aqueous bleed stream having being reduced in UV-absorbing and other impurities, acids and ions as previously described, will have a second UV 220 nm transmittance significantly higher than the first UV 220 nm transmittance. For a cycle water treatment unit that contains a strong base anionic exchange resin, the second UV 220 nm transmittance is at least 50% higher, preferably at least 70% higher than the first UV 220 nm transmittance. For a cycle water treatment unit that contains a weak base anionic exchange resin, the second UV 220 nm transmittance is at least 25% higher than the first UV 220 nm transmittance. By contrast, as expected the transmittance at UV 350 nm is barely changed, with the second UV 350 transmittance being at most 20% higher than the first UV 350 transmittance regardless of the resin used. The measurement of the UV transmittance; the action and physical mechanisms of the ion exchange beds or resins, especially the anion exchange resin; and further details regarding the ion exchange resins are discussed in greater detail below.

While for the purposes of this invention it is the measurement of the transmittance at UV 220 nm that is used to regulate and control the presence of product quality-impairing impurities in the aqueous bleed stream, other measurements of the aqueous bleed stream—such as pH and conductivity, can also be made as described in greater detail below. A low conductivity measurement demonstrates the resin is removing dissociated ions by ion exchange in addition to removing organic impurities such as aldehydes. Thus, the aqueous bleed stream entering the cycle water treatment unit will have a first conductivity lower than a second conductivity measured of the treated bleed stream with the additional provision that the second conductivity will be less than 5 μS/cm, wherein "S" is siemens, i.e., the SI derived unit of electric conductance.

After leaving the cycle water treatment unit, the treated aqueous bleed stream may be subjected to further treatment or processing or preferably sent to the ethylene glycol purification section of an ethylene oxide/ethylene glycol plant. As long as the impurity level has been sufficiently reduced so that the aqueous stream may be then be further processed without damaging the plant or the product quality, then this aqueous stream may be sent back to the plant, such as the ethylene glycol purification section of the plant.

Ion Exchange Resins

As discussed above, the cycle water treatment unit of the present invention contains at least one anion exchange treatment resin, but may contain additional resin beds as well. Ion exchange resins have a polymer matrix which contains on the surface ion exchanging sites populated by ionic functional groups. Ion exchange resins are typically differentiated between cationic or anionic exchange resins, although other types of ion exchange resins are also available. Without being limited by theory, it is believed that the retention of impurities such as soluble organics and associated acids from the lean cycle water by anion exchange resin involves both ion exchange and physical—van der Waal's forces. The resin not only exchanges dissociated ions and inorganic salts but also exchanges and absorbs organics. The organic molecules diffuse slowly into the anion resin and are held within the resin matrix. The van der Waal's force bonding is the main mechanism for adsorption of the organic molecules on the resin.

Suitable polymer matrices for the ion exchange bed include a polystyrene matrix, a polyacrylic matrix, a polyalkylamine resin as well as others polymeric materials. Preferably, the polymer matrix is cross-linked with divenylbenzene to a sufficient degree to increase the operating capacity while also not increasing the density of the ion exchange material to such an extent that the ion exchange material becomes too physically hard and too chemically resistant to chemical treatment. Preferably the matrix is a styrene, divenylbenzene co-polymer. In addition to the aforementioned structures, alternative materials and structures may also be used such as macroporous resins and natural ion exchange materials such as clay and zeolite minerals.

Preferably the present resins have a minimum total exchange capacity of 1 milliequivalent/ml of resin. Preferably the resins have a 95% particle size distribution in the range of 0.3 to 1.2 mm.

Disposed on the active sites of the ion exchange resin are ionic functional groups that determine whether the resin functions as a cationic or anionic ion exchange resin. In solutions, the positive or negative charge of the stationary groups is compensated for by ions of opposite charge. Strongly acidic cationic ion exchange resins typically include sulfonic groups. Examples of strongly acidic sulfonic cation-exchange resins include Amberlite IR 120, Dowex HCR, Lewatit S 100, and Amberlyst 15, among others. Weakly acidic cationic ion exchange resins typically include carboxylic groups. Examples of weakly acidic cation-exchange resins include Amberlite IRC 86, and Lewatit CNP, among others. Further examples of suitable cation-exchangers include the Tulsion T56MP and TG 057 cation exchanger from Thermax LTD, Pune, India.

Suitable anion-exchange resins include chloromethylated polystyrene which can be made in a variety degrees of basicity and include various Amberlite grades such as IRA 402, IRA 410, and IRA 96. Weak Anion exchange resins can also include polyacrylic resins provided with functional groups by reaction with a polyfunctional amine to result in an anion exchange resins such as the tertiary weakly basic Amberlite IRA 67 and Amberlyst A21 or then further treated with chloromethane or dimethyl sulfate to give a quaternary amine strongly basic resin IRA 458. Further examples of suitable anion exchange resins include, Tulsion A8X MP and A9X MP anion exchangers from Thermax LTD and those anion exchange resins disclosed in U.S. Pat. No. 6,187,973, herein incorporated by reference.

As used herein in the present invention, strongly basic anionic exchange resins contain quaternary ammonium stationary groups. These are further divided into Type I, made by the reaction of trimethylamine with the styrene-divenylbenzene copolymer after chloromethylation, and Type II obtained by the reaction of the styrene-divenylbenzene copolymer with dimethylethanolamine. Suitable examples of such Type I resins include Lewatit M 500 available from Lanxess, and Amberlyst 26 and Amberlite IRA 402, and IRA 410 available from Dow and Trilite AMP16 from Samyong-Mitsubishi. Purolite A510S (Purolite Corporation) is a suitable example of strongly basic Type II resin.

Weakly basic anion exchange resins typically include polyacrylic resins provided with stationary groups by reaction with a polyfunctional amine to result in anion exchange resins such as the tertiary amine weakly basic Amberlite IRA 67 and Amberlyst 21 resins (available from Dow Weakly basic anion exchange resins may also include a free base group as the stationary group such as the Amberlite IRA-67 resin (Dow). Further commercially available suitable weakly basic anion resins include Trilite AW90 from Samyong-Mitsubishi, Purolite A103S Plus (Purolite Corporation), and Lanxess Lewatit 54228. Weak base resins function particularly well as acid adsorbers. They have a high adsorption capacity and can be readily regenerated with caustic. They are particularly useful when combined a strong base anion to act as a polishing bed to present the strong base anion resin from organic fouling.

In addition to the specified ion exchange materials specified above, any other suitable cationic or anionic exchange resin may be used such as the cation- and anion-exchange resins set forth in de Dardel, F. and Arden, T. V. 2008, *Ion Exchanger*, in Ullman's *Encyclopedia of Industrial Chemistry*.

Ion Exchange Regeneration

As mentioned above, when not in use, the ion exchange treatment beds can either be in stand-by mode or undergoing regeneration in the event of exhaustion. Regeneration occurs by washing the solid adsorbent and ion exchange resin with a regenerant to remove and displace the impurities and ions adsorbed by the resin and replenish at the active sites on the resin the respective counter-ions released by the resin into the solution, thus restoring the ability of the resin to capture and adsorb ions and impurities. During regeneration, these impurities, ions and other organics elute and are released into the liquid regenerant. The regenerant should be specifically selected to replenish the ions on the surface of the ion exchange resin—for example sodium hydroxide regenerate is preferred for regenerating an anion bed with hydroxide functional groups in particular for replenishing the hydroxide that has been released by the resin during service. Similarly, for a cation resin with hydrogen ion functional groups, regeneration is typically accomplished by the use of HCl or sulfuric acid as the regenerant. Other typical regenerants include sodium sulfate. The regenerate level or concentration of regenerant is typically selected for ease of supply at commercial scale. An example of a suitable regenerant for anion bed is a 4-5 wt % solution of sodium hydroxide.

During regeneration the regenerant may either flow in the opposite direction of the service flow ("Counter-Current Regeneration) or the regenerant flows in the same direction of the service flow (Co-Current Regeneration). Co-Current Regeneration is more typically used for regenerating ion exchange beds; however, Counter-Current Regeneration is particularly useful for strongly acidic resins that suffer from the problem that under Co-Current Regeneration they are not completely converted to the H or OH form at the end of regeneration, because of the extremely high volumes of regenerant that would require too large an excess of chemical regenerant. As a result, the bottom layer at the end of regeneration is still loaded with contaminants, so that when the ion exchange resin is returned to service there is a higher level of breakthrough due to the displacement of the contaminating ions by the $H^+$ (or $OH^-$) ions. It is believed that such problems can be mitigated with counter-current regeneration.

Typically regeneration is followed by a rinsing cycle with demineralized water to displace the regenerant from the ion exchange bed. This rinsing may be accomplished in one or more cycles, with each cycle conducted under different parameters, like flow rate. At the completion of the rinsing step, the ion exchange bed should be free of regenerant.

Degasifier

In addition to the aforementioned ion exchange treatment beds, a vacuum degasifier (not shown) may be used to reduce the free carbon dioxide in a stream to levels of a few ppm. The system may be designed with or without a vacuum degasifier depending on the preferences of the user. The degasifier functions by removing carbon dioxide from the aqueous stream. Because carbon dioxide is a relatively weak acid, by removing it from the aqueous stream, then a weak base may be used for removal of the remainder of the impurities instead of a strong base since carbon dioxide does not need to be removed from the aqueous stream. The use of a weak base resin rather than a strong base resin reduces the amount of chemicals needed for regeneration. Thus, the degasifier increases capital costs (the cost of the degasifier increases capital costs) while reducing operating costs (less chemicals for regeneration lowers the operating cost). Thus, the selection of which of these options is up to the individual end user.

Analyzer Units

UV analyzers are placed at the various outlet streams especially the outlet of the cycle water treatment unit to provide continuous online measurement of the performance of the ion exchange treatment beds in removing impurities.

As described above, in the present invention the measurement of the concentration of the impurities in the aqueous bleed stream is measured by UV transmittance, specifically by monitoring the transmittance before and after treatment in the cycle water treatment unit at the UV 220 nm level. If the aqueous bleed stream fails to meet certain minimum UV transmittance percentages, then it will be of insufficient quality to qualify as fiber grade and hence the value of it as ethylene glycol will be much reduced. The UV transmittance value in the aqueous bleed stream at breakthrough is as follows:

TABLE I

| Wave Length (nm) | Transmittance %, minimum |
| --- | --- |
| 220 | 85 |

When the UV 220 transmittance of the treated aqueous bleed stream starts to approach these minimum values, this indicates that the capacity of the ion exchange resins of the lean cycle water treatment unit to adsorb impurities from the aqueous ethylene glycol solution has been reached and it needs to be regenerated. The UV 220 transmittance is useful in measuring the concentration of non-ionic impurities that are especially important to remove like aldehydic impurities as well as other components such as the glycol ester forms of formic acid (ethylene glycol monoformate) and acetic acid (ethylene glycol monoacetate). UV 220 transmittance is also a useful measurement because it is a typical product specification for ethylene glycol—an ethylene glycol-containing stream leaving the treatment unit that meets the appropriate UV 220 transmittance level will contribute positively to the final purified ethylene glycol product meeting this specification.

As a supplement to the UV analyzer, other suitable analytical techniques may be used in this application, including measurement of the conductivity or pH (which are functionally the same measurement). Conductivity can be used to measure the concentration of impurities in the stream because water, as a non-electrolyte, is generally a poor conductor. However, as a result of electrolytic dissociation, acids, bases and other impurities dissociate in the water into ions allowing determination of the electrolytic content of the water. Thus, strong and weak electrolytes can be differentiated based on their degree of dissociation. However, conductivity is not effective for measuring the UV 220 absorbing impurities that are the subject of the present invention and thus, cannot replace UV 220 measurements as presently conceived.

Having been treated in the lean cycle water treatment unit, the treated aqueous stream is preferably sent to the glycol purification section of the plant, where the ethylene glycol is separated from the treated water (and the glycol purified) and the now glycol-free water sent as recycle water to the glycol reactors.

Silver-Based Epoxidation Catalyst

The silver-based epoxidation catalyst includes a support, and at least a catalytically effective amount of silver or a silver-containing compound; also optionally present is a promoting amount of rhenium or a rhenium-containing compound; also optionally present is a promoting amount of one or more alkali metals or alkali-metal-containing compounds. The support employed in this invention may be selected from a large number of solid, refractory supports that may be porous and may provide the preferred pore structure. Alumina is the most preferable refractory support material.

In general, a suitable catalyst support of the present invention can be prepared by mixing the refractory material, such as alumina; water or other suitable liquid; a burnout material or suitable porosity-controlling agent; and a binder. Burnout materials include cellulose, substituted celluloses, e.g. methylcellulose, ethylcellulose, and carboxyethylcellulose, stearates, such as organic stearate esters, e.g. methyl or ethyl stearate, waxes, granulated polyolefins, particularly polyethylene and polypropylene, walnut shell flour, and the like which are decomposable at the firing temperatures used in preparation of the support. The burnout is used to modify the porosity of the support. It is essentially totally removed during the firing to produce the finished support. Supports of the present invention are preferably made with the inclusion of a bonding material such as silica with an alkali metal compound in sufficient amount to substantially prevent the formation of crystalline silica compounds. Appropriate binders include inorganic clay-type materials. A particularly convenient binder material is a mixture of boehmite, an ammonia stabilized silica sol, and a soluble sodium salt.

A paste is formed by mixing the dry ingredients of the support with water or other suitable liquid, and the paste is usually extruded or molded into the desired shape, and then fired or calcined at a temperature of from about 1200° C. to about 1600° C. to form the support. When the particles are formed by extrusion, it may be desirable to also include extrusion aids. The amounts of extrusion aids required would depend on a number of factors that relate to the equipment used. However, these matters are well within the general knowledge of a person skilled in the art of extruding ceramic materials. After firing, the support is preferably washed to remove soluble residues. Washing is most commonly done with water but washing with other solvents or aqueous/non-aqueous solutions can also be beneficial. Suitable supports having a bimodal pre-distribution are available from Saint-Gobain Norpro Co., Noritake Co., and Clariant Corporation, CeramTec AG.

The support preferably has a B.E.T. surface area of at most 5 $m^2/g$, and more preferably at most 2 $m^2/g$. More preferably, the B.E.T. surface area is in the range of 0.4-4.0 $m^2/g$, more preferably from about 0.5 to about 1.5 $m^2/g$. Preferably, the support comprises alumina with a surface area of less than about 2 $m^2/g$. The B.E.T. surface area described herein can be measured by any suitable method, but is more preferably obtained by the method described in Brunauer, S., et al., J. Am. Chem. Sac, 60, 309-16 (1938). Suitable porosity volumes measured by mercury intrusion techniques are expected to be in the range of from about 0.2 $m^2/g$ to about 0.8 ml/g, preferably from about 0.25 ml/g to about 0.60 $m^2/g$. The final support typically has a water absorption values ranging from about 0.2 cc/g to about 0.8 cc/g, preferably from about 0.25 cc/g to about 0.6 cc/g.

The carrier of the invention can be of any suitable shape or morphology. For example, the carrier can be in the form of particles, chunks, pellets, rings, spheres, three-holes, wagon wheels, cross-partitioned hollow cylinders, and the like, of a size preferably suitable for employment in fixed bed reactors. Typically, carrier particles have equivalent diameters in the range of from about 3 mm to about 12 mm, and more typically in the range of from about 5 mm to about 10 mm, which are usually compatible with the internal diameter of the tubular reactors in which the catalyst is placed. As known in the art, the term "equivalent diameter" is used to express the size of an irregularly-shaped object by expressing the size of the object in terms of the diameter of a sphere having the same volume as the irregularly-shaped object.

In order to produce a catalyst for the oxidation of an olefin to an olefin oxide, a support having the above characteristics is then provided with a catalytically effective amount of silver on its surface. In one embodiment, the catalytic effective amount of silver is from 10% by weight to 45% by weight. The catalyst is prepared by impregnating the support with a silver compound, complex or salt dissolved in a suitable solvent sufficient to cause deposition of a silver-precursor compound onto the support. Preferably, an aqueous silver solution is used.

A promoting amount of a rhenium component, which may be a rhenium-containing compound or a rhenium-containing complex may also be deposited on the support, either prior to, coincidentally with, or subsequent to the deposition of the silver. The rhenium promoter may be present in an amount from about 0.001 wt. % to about 1 wt. %, preferably from about 0.005 wt. % to about 0.5 wt. %, and more preferably from about 0.01 wt. % to about 0.1 wt. % based on the weight of the total catalyst including the support, expressed as the rhenium metal.

Other components which may also be deposited on the support either prior to, coincidentally with, or subsequent to the deposition of the silver and rhenium are promoting amounts of an alkali metal or mixtures of two or more alkali metals, as well as optional promoting amounts of a Group IIA alkaline earth metal component or mixtures of two or more Group IIA alkaline earth metal components, and/or a transition metal component or mixtures of two or more transition metal components, all of which may be in the form of metal ions, metal compounds, metal complexes and/or metal salts dissolved in an appropriate solvent. The support may be impregnated at the same time or in separate steps with the various catalyst promoters. The particular combination of support, silver, alkali metal promoter(s), rhenium component, and optional additional promoter(s) of the instant invention will provide an improvement in one or more catalytic properties over the same combination of silver and support and none, or only one of the promoters.

As used herein the term "promoting amount" of a certain component of the catalyst refers to an amount of that component that works effectively to improve the catalytic performance of the catalyst when compared to a catalyst that does not contain that component. The exact concentrations employed, of course, will depend on, among other factors, the desired silver content, the nature of the support, the viscosity of the liquid, and solubility of the particular compound used to deliver the promoter into the impregnating solution. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished.

Suitable alkali metal promoters may be selected from lithium, sodium, potassium, rubidium, cesium or combinations thereof, with cesium being preferred, and combinations of cesium with other alkali metals being especially preferred. The amount of alkali metal deposited or present on the support is to be a promoting amount. Preferably, the amount ranges from about 10 ppm to about 3000 ppm, more preferably from about 15 ppm to about 2000 ppm, and even more preferably from about 20 ppm to about 1500 ppm, and as especially preferred from about 50 ppm to about 1000 ppm by weight of the total catalyst, measured as the metal.

Suitable alkaline earth metal promoters comprise elements from Group IIA of the Periodic Table of the Elements, which may be beryllium, magnesium, calcium, strontium, and barium or combinations thereof. Suitable transition metal promoters may comprise elements from Groups IVA, VA, VIA, VIIA and VIIIA of the Periodic Table of the Elements, and combinations thereof.

The amount of alkaline earth metal promoter(s) and/or transition metal promoter(s) deposited on the support is a promoting amount. The transition metal promoter may typically be present in an amount from about 0.1 micromoles per gram to about 10 micromoles per gram, preferably from about 0.2 micromoles per gram to about 5 micromoles per gram.

The silver solution used to impregnate the support may also comprise an optional solvent or a complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, oxalic acid, lactic acid and combinations thereof. Amines include an alkylene diamine having from 1 to 5 carbon atoms. In one preferred embodiment, the solution comprises an aqueous solution of silver oxalate and ethylene diamine. The complexing/solubilizing agent may be present in the impregnating solution in an amount from about 0.1 to about 5.0 moles per mole of silver, preferably from about 0.2 to about 4.0 moles, and more preferably from about 0.3 to about 3.0 moles for each mole of silver.

When a solvent is used, it may be an organic solvent or water, and may be polar or substantially or totally non-polar. In general, the solvent should have sufficient solvating power to solubilize the solution components. At the same time, it is preferred that the solvent be chosen to avoid having an undue influence on or interaction with the solvated promoters. Organic-based solvents which have 1 to about 8 carbon atoms per molecule are preferred. Mixtures of several organic solvents or mixtures of organic solvent(s) with water may be used, provided that such mixed solvents function as desired herein.

The concentration of silver in the impregnating solution is typically in the range from about 0.1% by weight up to the maximum solubility afforded by the particular solvent/solubilizing agent combination employed. It is generally very suitable to employ solutions containing from 0.5% to about 45% by weight of silver, with concentrations from 5 to 35% by weight of silver being preferred.

Impregnation of the selected support is achieved using any of the conventional methods; for example, excess solution impregnation, incipient wetness impregnation, spray coating, etc. Typically, the support material is placed in contact with the silver-containing solution until a sufficient amount of the solution is absorbed by the support. Preferably the quantity of the silver-containing solution used to impregnate the porous support is no more than is necessary to fill the pores of the support. A single impregnation or a series of impregnations, with or without intermediate drying, may be used, depending, in part, on the concentration of the silver component in the solution. Impregnation procedures are described, for example, in U.S. Pat. Nos. 4,761,394, 4,766,105, 4,908,343, 5,057,481, 5,187,140, 5,102,848, 5,011,807, 5,099,041 and 5,407,888. Known prior procedures of pre-deposition, co-deposition and post-deposition of various the promoters can be employed.

After impregnation of the support with the silver-containing compound, i.e., a silver precursor, a rhenium component, an alkali metal component, and the optional other promoters, the impregnated support is calcined for a time sufficient to convert the silver containing compound to an active silver species and to remove the volatile components from the impregnated support to result in a catalyst precursor. The calcination may be accomplished by heating the impregnated support, preferably at a gradual rate, to a temperature in the range from about 200° C. to about 600° C. at a pressure in the range from about 0.5 to about 35 bar. In general, the higher the temperature, the shorter the required heating period. A wide range of heating periods have been suggested in the art; e.g., U.S. Pat. No. 3,563,914 discloses heating for less than 300 seconds, and U.S. Pat. No. 3,702,259 discloses heating from 2 to 8 hours at a temperature of from 100° C. to 375° C., usually for duration of from about 0.5 to about 8 hours. However, it is only important that the heating time be correlated with the temperature such that substantially all of the contained silver is converted to the active silver species. Continuous or step-wise heating may be used for this purpose.

During calcination, the impregnated support may be exposed to a gas atmosphere comprising an inert gas or a mixture of an inert gas with from about 10 ppm to 21% by volume of an oxygen-containing oxidizing component. For purposes of this invention, an inert gas is defined as a gas that does not substantially react with the catalyst or catalyst precursor under the conditions chosen for the calcination. Further information on catalyst manufacture may be found in the aforementioned U.S. Patent Publication No. 2007/0037991.

EXAMPLES

The invention will now be described in more detail with respect to the following non-limiting examples.

Figure 2:
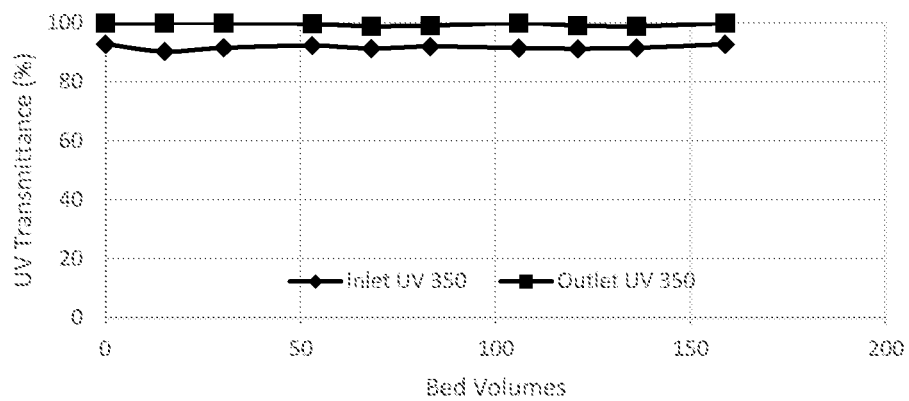
FIG. 2 shows the 350 nm transmittance values of the aqueous bleed stream measured at the inlet and outlet of the cycle water treatment unit in the same plant as referenced above with respect to FIG. 1.

An ethylene oxide/ethylene glycol plant capable of annual production of greater than 250,000 MT EOE ("ethylene oxide equivalent") was operated as described above with the reactor effluent contacted with lean cycle water to produce rich cycle water and the rich cycle water stripped of its ethylene oxide in a stripping column and a bleed stream taken from the lean cycle water. The bleed stream was sent to a cycle water treatment unit containing a weak base anion exchange resin. FIGS. 1 and 2 show the UV of the bleed stream measured at the inlet and outlet of the treatment unit measured at two separate wavelengths: 220 nm and 350 nm. By comparing these two measurements reflect the UV improvement across the resins. In FIGS. 1 and 2, the abscissa is bed volume processed and the ordinate is % transmission; inlet transmission is the lower line and outlet transmission is the higher line. Bed Volume per hour is defined as the measure of the volume flow rate through an ion exchange material contained in the column.

It can be observed from FIGS. 1 and 2 that in an ethylene glycol process the transmittance of 220 nm wavelength measured at the inlet is significant lower than at 350 nm. This is indicative that the majority of the impurities in the ethylene glycol process absorbed 220 nm wavelength, while having little effect on longer wavelength transmittance. Similarly, after treatment there is little improvement in blead stream transmittance at 350 nm wavelengths further indicating that there was relatively small content of impurities that absorbed at those wavelengths. By contrast, at 220 nm transmittance improved by 56% from 40% to 96%.

FIGS. 3 and 4 and 5 and 6 show results from testing conducted in a pilot-sized treatment unit fabricated from a 3.0 m (11.5 foot) length of acrylic pipe with a 4 cm (1.5 inch) inside diameter by attaching a bottom support plate and appropriate valves and connections. The pipe was packed about half full of an anionic resin. The resin was well rinsed, backwashed, and regenerated with excess 5 wt % caustic solution. Excess caustic was rinsed away with deionized water prior to operation. The resin placed in the pipe was either a weak or a strong base anion resins. In the examples illustrated by FIGS. 3 and 4, the weak base anion resin was a macro-porous resin based on a polystyrene copolymer containing tertiary ammonium functional groups. In the examples illustrated by FIGS. 5 and 6, the strong base resin is a macro-porous type 1 polymeric resin based on cross-linked styrene divinylbenzene copolymer containing quaternary ammonium functional groups. Both resins have a 95% particle size distribution in the range of 0.3 to 1.2 mm and a minimum total exchange capacity of 1 milliequivalent/ml of resin.

A lean cycle water bleed stream having a low UV transmission was fed to the pipe at approximately 10 L/hour (9 L/h for WBA and 11 L/h for SBA). The 220 nm, 275 nm and 350 nm transmission of the bleed stream was measured at the bed inlet and outlet.

Figure 3:
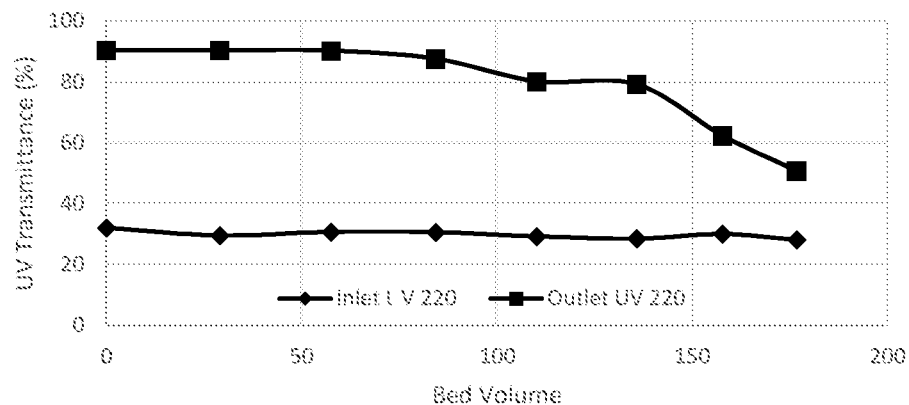
FIG. 3 shows the 220 nm transmittance values of the aqueous bleed stream measured at the inlet and outlet of a pilot-sized cycle water treatment unit containing a weak base resin.
Figure 4:
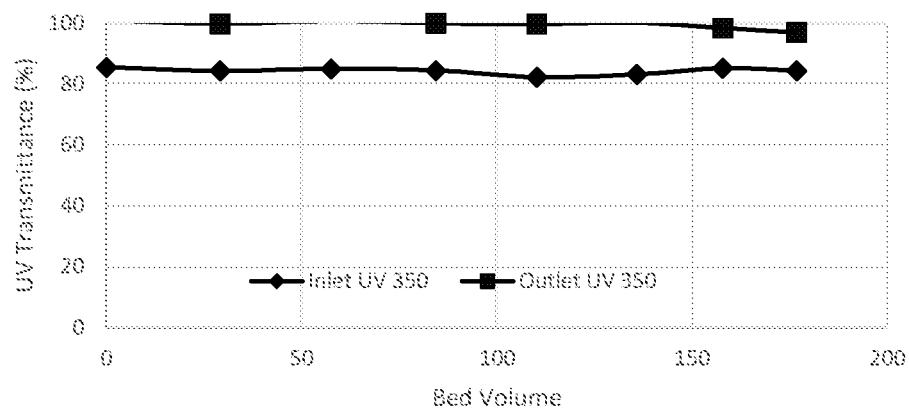
FIG. 4 shows the 350 nm transmittance values of the aqueous bleed stream measured at the inlet and outlet of the cycle water treatment unit containing a weak base resin.

FIG. 3 shows that the weak base anion resin improved transmittance (when fresh, BV=0) at UV 220 nm by 62% from 32% to 90%. FIG. 4 plots the data at UV 350 nm—again as above with respect to FIG. 2, this plot shows that the majority of the impurities in the ethylene glycol process absorbed 220 nm wavelength and after treatment there is little improvement in bleed stream transmittance at the 350 nm wavelength further indicating that there was relatively little content of impurities that absorbed at that wavelength.

Figure 5:
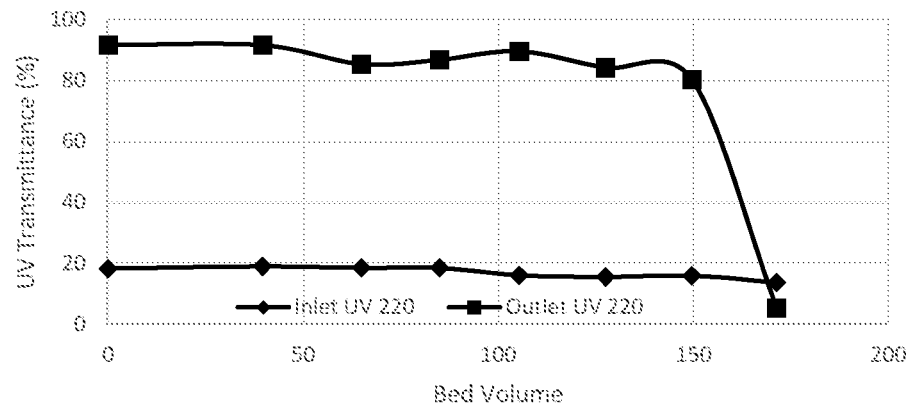
FIG. 5 shows the 220 nm transmittance values of the aqueous bleed stream measured at the inlet and outlet of the cycle water treatment unit containing a strong base resin.
Figure 6:
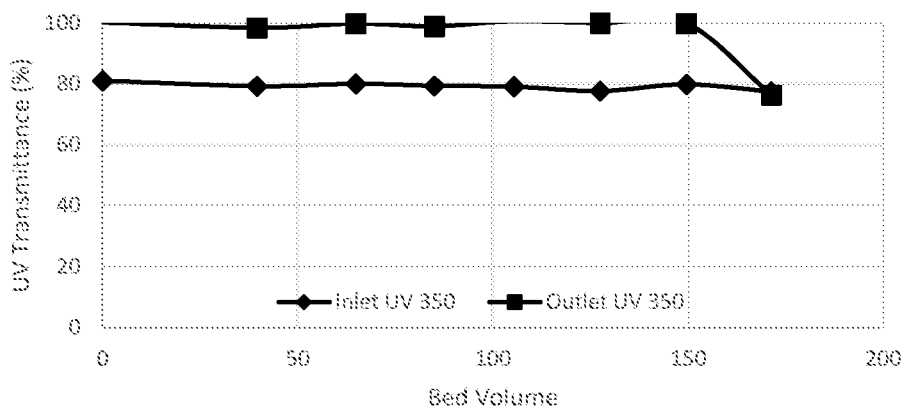
FIG. 6 shows the 350 nm transmittance values of the aqueous bleed stream measured at the inlet and outlet of the cycle water treatment unit containing a strong base resin.

FIGS. 5 and 6 demonstrate the same effects at UV 220 nm and UV 350 nm as illustrated above but in this case with a strong base anion resin. FIG. 5 shows that the strong base anion resin improved transmittance (when fresh, BV=0) at UV 220 nm by even more than the weak base anion resin, the improvement from the strong base anion resin was 74% from 18% to 92%.

Figure 7:
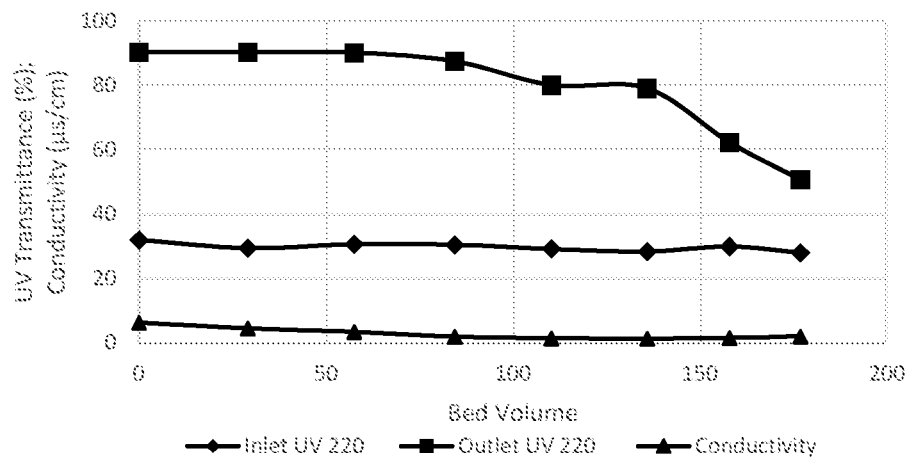
Figure 8:
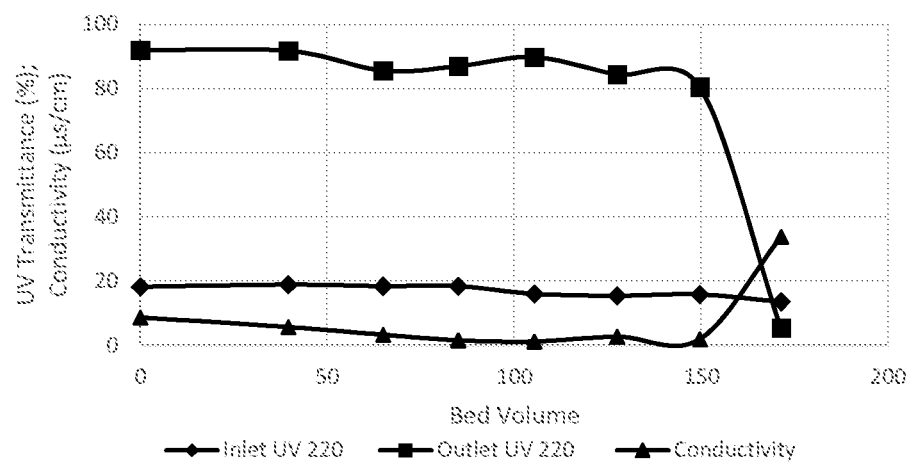
FIG. 8 shows the 350 nm 220 nm transmittance values of FIG. 5 with the addition of conductivity data measured and plotted for comparison.

For comparison across analytical techniques, the conductivity was also measured and is plotted alongside the UV 220 nm transmittance measurements in FIGS. 7 and 8. FIG. 7 replots the same data from FIG. 3 but with the conductivity measurement added. FIG. 8 replots the same data from FIG. 5, but with the conductivity measurement added. The value plotted is the conductivity of the lean cycle water bleed stream measured at the outlet of the treatment unit. As can be seen the conductivity value is extremely low showing that the resin is performing its usual function of catalyzing ion exchange between dissociated ions and organic acids and the ion exchange resin. This is in addition to the uptake of organics such as aldehydes, and esters of formic and acetic acid.

It will be appreciated by those skilled in the art that changes could be made to the embodiments described above without departing from the broad inventive concept thereof. It is understood therefore that this invention is not limited to the particular embodiments disclosed, but it is intended to cover modifications within the spirit and scope of the present invention as defined by the appended claims.

What we claim is:

1. A method for removing impurities from an ethylene oxide manufacturing plant, the method comprising:
   providing an aqueous bleed stream comprising 0.2 to 20 wt % ethylene glycol and having a first UV 220 nm transmittance; and
   introducing the aqueous bleed stream to a cycle water treatment unit containing an anion exchange resin to reduce the content of impurities in the aqueous bleed stream, wherein the aqueous bleed stream at an outlet of the cycle water treatment unit has a second UV 220 nm transmittance and the second UV 220 nm transmittance is higher than the first UV 220 nm transmittance, wherein the anion exchange resin is a strong base anion exchange resin having a minimum total exchange capacity of 1 milliequivalent/ml of resin and a 95% particle size distribution in the range of 0.3 to 1.2 mm.

2. The method according to claim 1, wherein the second UV 220 nm transmittance is at least 50% higher than the first UV 220 nm transmittance.

3. The method according to claim 1, wherein the second UV 220 nm transmittance is at least 70% higher than the first UV 220 nm transmittance.

4. The method according to claim 1, wherein the strong base anion exchange resin is prepared by by reacting styrene-divinylbenzene copolymer with dimethylethanolamine.

5. The method according to claim 1, wherein the second UV 220 nm transmittance is at least 25% higher than the first UV 220 nm transmittance.

6. The method according to claim 1, wherein the aqueous bleed stream has a first conductivity and the outlet the cycle water treatment unit has a second conductivity, the second conductivity being lower than the first conductivity and the second conductivity having a value of less than 5 µS/cm.

7. The method according to claim 1, wherein the aqueous bleed stream has a first UV 350 nm transmittance, and the outlet the cycle water treatment unit has a second UV 350 nm transmittance, wherein the second UV 350 nm transmittance is at most 20% higher than the first UV 350 nm transmittance.

8. The method according to claim 1, wherein the impurities are selected from long chain esters, formaldehyde, acetaldehyde, glycolaldehyde and their associated acids and ions, and mixtures thereof.

9. The method according to claim 1, wherein the cycle water treatment unit is operated at a temperature from about 30° C. to about 50° C.

10. The method according to claim 1, further comprising initiating an epoxidation reaction by reacting a feed gas composition containing ethylene and oxygen in the presence of an epoxidation catalyst comprising a promoting amount of rhenium.

11. The method according to claim 10, wherein the impurities are selected from long chain esters, formaldehyde, acetaldehyde, glycolaldehyde and their associated acids and ions, and mixtures thereof.

* * * * *